> United States Patent [19]

Gray

[11] 4,422,961
[45] Dec. 27, 1983

[54] RANEY ALLOY METHANATION CATALYST

[75] Inventor: Thomas J. Gray, Guilford, Conn.

[73] Assignee: Olin Corporation, New Haven, Conn.

[21] Appl. No.: 364,576

[22] Filed: Apr. 1, 1982

Related U.S. Application Data

[62] Division of Ser. No. 353,534, Mar. 1, 1982.

[51] Int. Cl.³ .............................................. B01J 25/02
[52] U.S. Cl. .................................. 502/301; 502/527; 502/315; 502/326; 502/327
[58] Field of Search ................. 252/466 J, 477 Q, 465, 252/470, 472; 427/247

[56] References Cited

U.S. PATENT DOCUMENTS

| Re. 31,104 | 12/1982 | Baldi et al. | 252/477 Q |
| 3,674,710 | 7/1972 | Richter et al. | 252/465 |
| 3,781,227 | 12/1973 | Sokolsky et al. | 252/477 Q |
| 4,043,946 | 8/1977 | Sanker et al. | 252/466 J |
| 4,289,650 | 9/1981 | Gray | 252/477 Q |

OTHER PUBLICATIONS

Baird et al., "Methanation Studies on Nickel-Aluminum Flame-Sprayed Catalysts", Product Research Development, vol. 16, No. 2, pp. 142-147, (1977).

*Primary Examiner*—W. J. Shine
*Attorney, Agent, or Firm*—Arthur E. Oaks; Donald F. Clements

[57] ABSTRACT

A methanation process utilizing an improved catalyst for the conversion of CO, $CO_2$ and mixtures thereof to $CH_4$ is disclosed. The catalyst comprises a monolithic mesh type structure of a nickel alloy having an integral Beta phase Raney coating on its outer surfaces. When used, substantially higher reactant flow rates and lower operating temperatures are possible as compared to conventional fluidized bed granular catalysts.

10 Claims, 8 Drawing Figures

ALUMINIZED MESH AFTER NaOH LEACH

RANEY ALLOY METHANATION CATALYST

This is a division, of application Ser. No. 353,534, filed Mar. 1, 1982.

FIELD OF THE INVENTION

The present invention is an improved catalyst for use in a process and apparatus for the production of methane from gases containing carbon monoxide, carbon dioxide or mixtures thereof and hydrogen.

BACKGROUND OF THE INVENTION

"Methanation" is a catalytic reaction which yields methane gas from carbon monoxide, carbon dioxide or mixtures thereof and hydrogen according to the equations:

$$CO + 3H_2 = CH_4 + H_2O, \Delta H = -52.7 \text{ Cal} \quad (1)$$

$$CO_2 + 4H_2 = CH_4 + 2H_2O, \Delta H = -43.6 \text{ Cal} \quad (2)$$

The limited availability of methane from natural sources coupled with the enormous utility of methane as a clean, sulfur free fuel have combined to create a great need for "synthetic natural gas". Methane made by methanation holds great economic significance because the reactants can be obtained by a reaction involving readily available coal with steam according to the basic equations:

$$2C + 2H_2O = 2CO + 2H_2 \quad (3)$$

and $$CO + H_2O = CO_2 + H_2 \quad (4)$$

to produce $$2C + 3H_2O = CO_2 + CO + 3H_2 \quad (5)$$

Reactions (1) and (2) are highly exothermic and are reversible so that high temperatures tend to reduce the yield of methane. Accordingly, heat removal poses a significant problem in all methanation processes. In addition, many of the processes either do not convert carbon dioxide to methane or are sensitive to the presence of sulfur compounds and/or an excessive amount of water in the process gases.

Conventional prior art methanation processes are conducted by usually passing the gaseous reactants through a packed or fluidized bed of a catalyst which is typically nickel or a nickel alloy with platinum. Such a process is disclosed, for example, in U.S. Pat. No. 3,930,812 issued to Harris et al. However, packed bed processes such as that of Harris et al are characterized by temperature control problems and a large pressure drop across the reactor. Dorschner et al, in U.S. Pat. No. 2,662,911, conduct the reaction in a plurality of catalyst packed tubes vertically arranged in a water-containing drum. Dorschner, in U.S. Pat. No. 2,740,803, also discloses methanation in a fluidized bed provided with double-wall bayonette type heat exchangers. This latter Dorschner patent also discloses an embodiment wherein the catalyst is contained in "contact tubes, vertically arranged in a water-containing drum having diameters which progressively decrease from the top to the bottom". These methods, like the more conventional packed bed methods, are also characterized by high pressure drops across the reactor.

Further, in most, if not all, of the foregoing prior art methanation processes characterized by the use of granular or particulate catalysts, there is a tendency to form coke on their surfaces and plug up over prolonged periods of time.

Lastly, it is known to use Raney nickel as a catalyst in methanation processes. See, for example, "Methanation Studies on Nickel-Aluminum Flame Sprayed Catalysts" by Baird and Steffgen, Journal of Industrial Engineering Chemistry, Product Research Development, Volume 16, No. (1977), in which the use of a methanation catalyst prepared by flame spraying aluminum onto a nickel surface followed by heating to form a Raney-type alloy and then activating it with a caustic leach is discussed. In this article, it was found that there was a strong correlation between the $NiAl_3$ (beta nickel) content in the unleached alloy and the methanation activity of the leached catalyst. No mention of the use of molybdenum, titanium, tantalum or ruthenium as alloying ingredients of the nickel is given or suggested.

Additional studies involving nickel-molybdenum methanation catalysts were reported by Wilhelm, Tsigdinos and Fernece, "Preparation and Activity of Nickel-Molybdenum Methanation Catalysts"; Chemical Uses of Molybdenum Proceedings, 3rd International Conference (1979). However, no mention of Raney treatment is given or suggested. When these catalysts were used even at elevated temperatures and pressures, useful CO conversions were reported to be in the neighborhood of only 80 to 90 percent. No suggestion of applicability to $CO_2$ is given.

Most recently, U.S. Pat. No. 4,043,946 issued to Sanker et al discloses a method for making a supported Raney nickel catalyst containing up to 5 percent molybdenum which, when tested for methanation activity, was found to require a temperature on the order of 320° C. to achieve a CO conversion of about 99 percent. No mention is made of potential applicability to $CO_2$.

SUMMARY OF THE INVENTION

The present invention provides an improved monolithic Raney methanation catalyst for use in a high velocity methanation reaction wherein hydrogen is reacted with a carbon-bearing oxide selected from the group consisting of CO, $CO_2$ and mixtures therof to form methane, said catalyst being of the type comprised of an integral Raney metal surface layer on a suitable substrate wherein said surface is predominantly derived from an adherent Beta structured crystalline precursory outer portion of said substrate.

Another embodiment of the invention is provided by the use of a monolithic Raney methanation catalyst of the type that comprises an integral Raney metal surface layer on a metallic mesh substrate, said Raney meta surface layer being predominantly derived from an adherent $Ni_xM_{1-x}Al_3$ Beta structured crystalline precursory surface layer, where M is a catalytic enhancer taken from a group consisting of the metals, molybdenum, titanium, tantalum and ruthenium and x, the weight fraction of nickel in the combined NiM alloy, is within the range of from about 0.80 to about 0.95.

The invention further comprises a method of using a Raney catalyst in a methanation reaction wherein said catalyst is produced by (a) coating with aluminum, the surfaces of a clean, non-porous perforated metal base structure of an alloy comprising from about 5 to about 20 percent by weight of a stabilizing metal selected from the group consisting of molybdenum, titanium, tantalum, or ruthenium, and from about 80 to about 95 percent by weight of nickel;

(b) heating said coated surfaces by maintaining said surfaces at a temperature of from about 660° C. to about 750° C. for a time sufficient to infuse a portion of said aluminum into outer portions of said structure to produce an integral alloy layer of nickel, the stabilizing metal and aluminum in said outer portions predominantly of Beta structured grains, but insufficient in time to create a predominance of Gamma structured grains in said outer portions; and (c) leaching out residual aluminum and intermetallics from the alloy layer until a Raney nickel alloy layer is formed integral with said structure.

These and other objects of the subject invention will become apparent from the following description and the appended claims.

DETAILED DESCRIPTION OF THE PREFERRED EMBODIMENT

This invention is described in terms of the preparation and use of a nickel alloy catalyst having about 5 to about 20 percent molybdenum therein. It should be understood that the molybdenum may be replaced in whole or in part by ruthenium, titanium or tantalum in the broader aspects of the invention.

Catalyst Preparation

Figure 1:
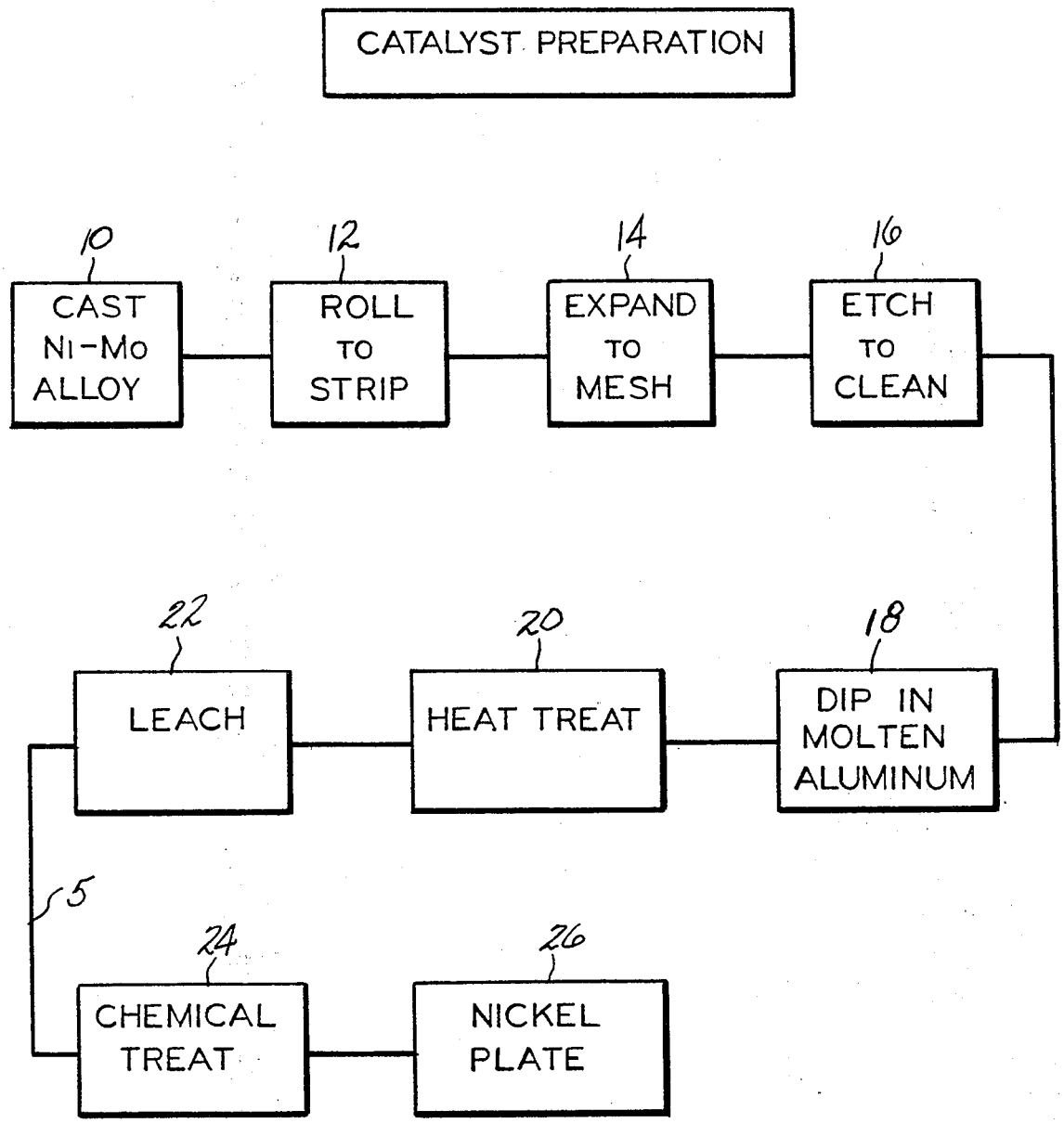
FIG. 1 is a flow diagram of a process for the preparation of an expanded mesh embodiment of the catalyst as used in the present invention.

Catalyst (5) of the present invention is prepared as shown in FIG. 1. The integral Raney nickel alloy surface of the monolithic catalyst (5) of this invention is formed on a supportive nickel bearing core or substrate. While cores of substantially pure nickel or an appropriate nickel bearing alloy such as Inconel 600, Hastelloy C or 310 stainless steel can be used, it is preferred to have the outer portions of the core (core is used interchangeably herein with substrate) itself serve as the nickel bearing alloy outer layer. Where cores of other materials or alloys are used, a nickel alloy coating of the desired composition should first be deposited onto the surfaces thereof by a variety of known techniques such as metal dipping, electroplating, electroless plating and the like. This coating should be at least 100 microns and preferably at least 150 microns thick. This helps to substantially improve the thermal stability of the coating by making the transition across the coating/substrate interface much less abrupt and thus greatly reducing tensile stresses and the possibility of corrosion and subsequent failure at this interface.

Accordingly, the core material for the catalyst of the present invention comprises an alloy in which nickel and the selected alloying material are melted together to form a precursor ingot (10) having the desired composition. When the alloying metal is molybdenum, the preferred weight percentage is between about 10 and about 18; for ruthenium, it is between about 5 and about 10 percent; for tantalum, it is between about 5 and about 15 percent and for titanium, it is between about 5 and about 10 percent. Thus it can be seen that in the preferred embodiments of the invention in the formula $Ni_xM_{1-x}Al_3$, x is between about 0.82 and about 0.90 when M is molybdenum;

x is between about 0.90 and about 0.95 when M is ruthenium;

x is between about 0.85 and about 0.95 when M is tantalum; and x is between about 0.90 and about 0.95 when M is titanium. The cast ingot is then rolled out to form a sheet or strip (12) preferably in the thickness range of between about 0.01 and about 0.02 inch.

While support for the catalyst of the current invention can be in the form of any conveniently shaped structure, a perforated metal base, particularly an expanded metal screen or mesh (14), is preferred. Such an open structure is found to be a significant factor in providing a catalytic process having substantial life-time and operational advantages over other types of catalytic structures used for this purpose. The final mesh which is prepared by conventional metal expansion techniques forms a regularly shaped diamond or square celled structure typically having cells on the order of 0.2 to 0.3 inch on a side. The thickness and mesh opening values are not critical and, depending on such factors as alloy composition and reaction parameters, other cell sizes could easily be used.

Prior to further processing, expanded mesh (14) is thoroughly cleaned by conventional means, such as degreasing, acid etching and/or grit blasting (16) to remove surface contaminates and thus improve the wetting of the subsequently applied aluminum to the surface.

Formation of the catalyst begins when this clean surface is subjected to an aluminizing treatment (18). By "aluminizing", as used herein, it is meant that aluminum is brought into intimate contact with the cleaned nickel bearing alloy material at the surface of the core so that when heat-treated at interdiffusion step (20), the desired nickel alloy-aluminum alloy layer is formed. This can be accomplished by any of several known methods such as flame or plasma spraying the aluminum onto the surface of the core, dipping the core into molten aluminum or by the use of fused salt electrolysis, with dipping being preferred.

Whichever method of aluminizing is used, an aluminum layer of at least 100-micron thickness should be deposited on the surface of the core. Much thicker aluminum layers of, for example, greater than 500-micron thickness, perform satisfactory in the process but for reasons for economy, aluminum layer thicknesses of between about 150 and about 300 microns are preferred. With dipping, such a thickness is achieved in a time of between about 0.5 and about 5.0 minutes when the aluminum is between about 600° C. and about 700° C.

Interdiffusion step (20) is carried out at a temperature of at least 660° C., i.e., above the normal melting point of aluminum. However, to drive the interdiffusion process at a reasonable rate, higher temperatures should be used, with the temperature within the range of from about 700° C. to about 750° C. and particularly from about 715° C. to about 735° C. being most preferred. Usually, interdiffusion is carried out in an atmosphere of hydrogen, nitrogen or an inert gas to prevent oxidation of the surface. This interdiffusion heat treatment is continued for a time sufficient for the aluminum and nickel alloy to react to form a nickel alloy-aluminum ternary alloy of at least 40 microns and preferably at least 80 microns in thickness. Interdiffusion times within the range of from about 5 to about 30 minutes satisfy this need. For nickel-molybdenum, interdiffused alloy layers of about 100 to about 400 microns in thickness are preferred, with best results obtained at between from about 150 to about 300 microns.

During heat treatment at temperatures above 660° C. excessively long interdiffusion times, e.g. 1 hour or more, and excessively high temperatures, should be avoided for technical as well as economic reasons. Thus, at temperatures above about 855° C., the Beta phase quickly transforms into liquid and Gamma phase. Further, if interdiffusion at any temperature is continued too long, all of the available aluminum can be diffused into the nickel resulting in a large excess of nickel in the interdiffused layer. Under these circumstances, especially at interdiffusion temperatures of much above about 800° C., an intermetallic NiAl (Eta) phase forms which is quite resistant to subsequent leaching of the aluminum so that a Raney nickel alloy surface will not form.

Lastly, for coatings on a substrate differing in composition from the coating, extended heat treatments might damage the substrate or form undesirable brittle intermetallics at the coating substrate interface. For example, if aluminum is diffused into a nickel alloy coated steel core, excessive interdiffusion time or temperature can result in the aluminum "breaking through" to diffuse into the steel base of the core. This results in the formation of a very brittle $FeAl_3$ intermetallic phase which will significantly undermine the strength of the bond between the core and the interdiffused layer.

By providing sufficient quantities of aluminum and nickel, while avoiding excessively long treatments or excessively high temperatures during interdiffusion, breakthrough and formation of the undesired intermetallics are avoided.

Figure 4:
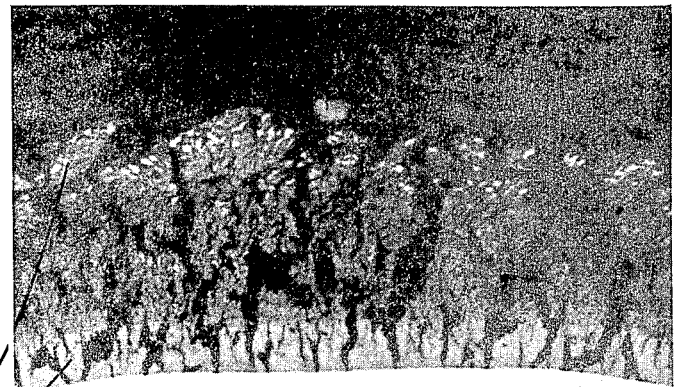
FIG. 4 is a 750x enlargement of a section of the Raney coating of FIG. 3.
Figure 3:
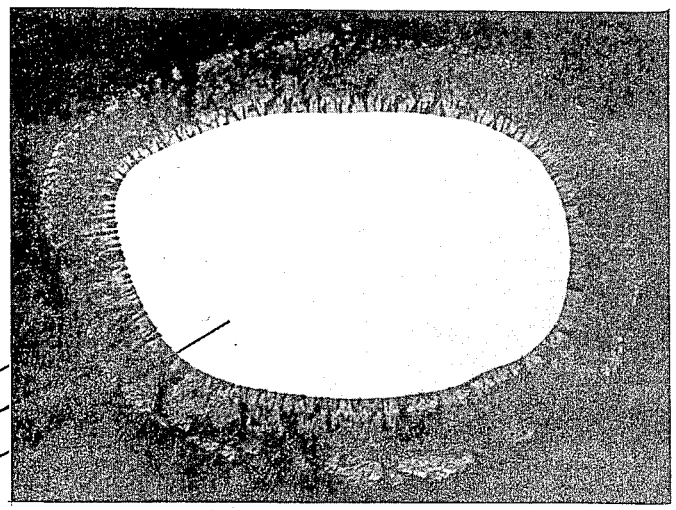
FIG. 3 is a 250x photomicrograph of a section of the mesh embodiment of the catalyst of FIG. 2 showing a Raney Ni-Mo layer after heat treatment and leaching.

The formation of the desired nickel-molybdenum-aluminum Beta structured ternary alloy layer is followed by a selective leaching step (22), wherein sufficient aluminum is removed to form an active nickel alloy surface layer. For this a strong aqueous base, such as NaOH, KOH or other strongly basic solution capable of dissolving aluminum, is generally used. Preferably, leaching is carried out with an aqueous caustic solution containing about 1 to about 30 weight percent NaOH. A preferred selective leaching procedure for producing porous nickel surfaces of the invention is carried out first for 2 hours with 1 percent NaOH, then for 20 hours with 10 percent NaOH, both of these substeps being under ambient conditions in which temperature is not controlled, and finally for 4 hours with 30 percent NaOH at 100° C. This leaching procedure removes at least about 60 percent and, preferably between about 75 to about 95 percent, of the aluminum from the interdiffused alloy layer and as shown in FIGS. 3 and 4 provides a porous nickel surface of unusually high catalytic activity. It is recognized that the leaching conditions can be varied from those mentioned above to achieve equally effective selective dissolution of the aluminum.

Figures 2, 5:
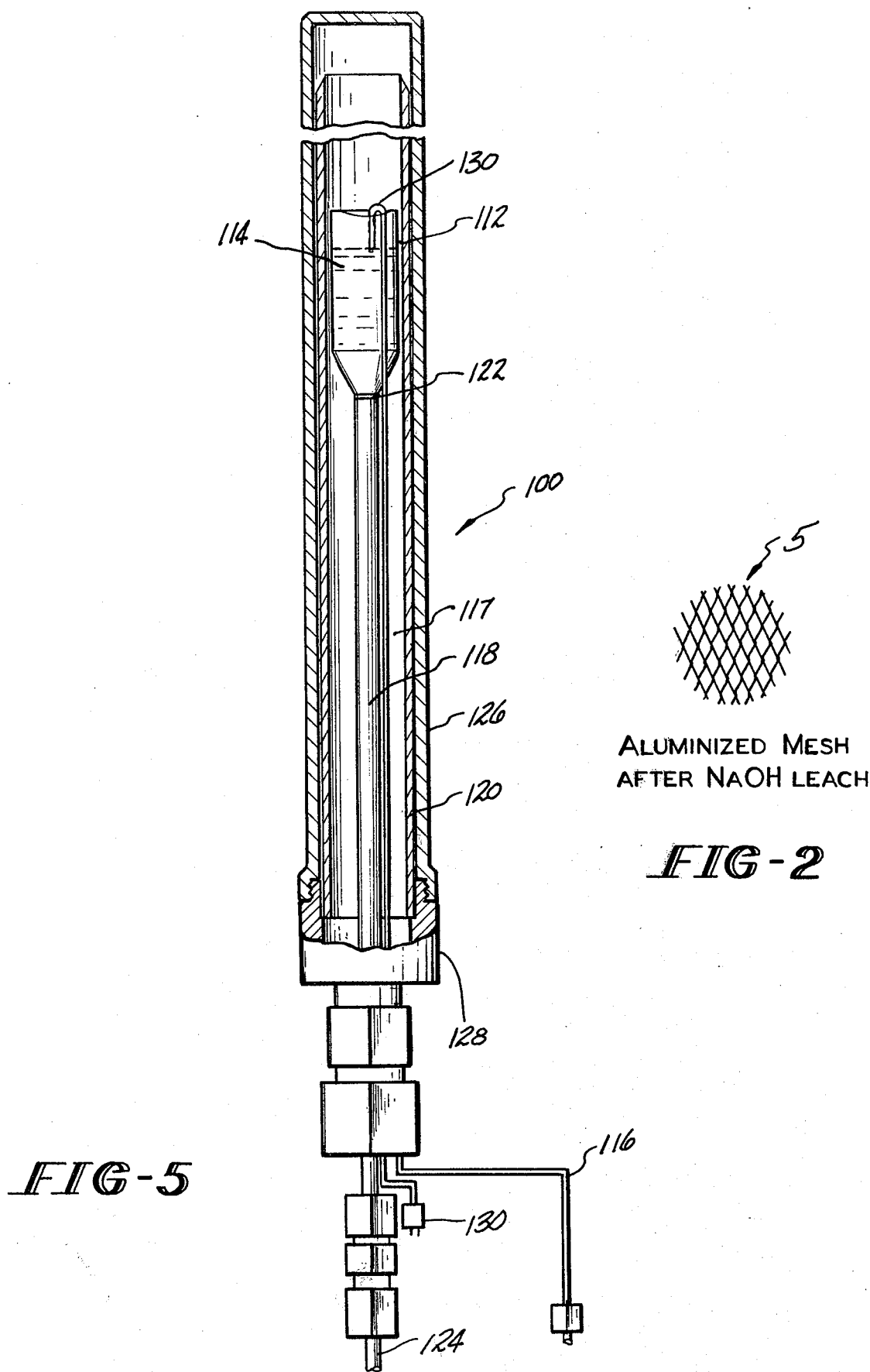
FIG. 2 shows the overall appearance of an expanded mesh embodiment of the catalyst of FIG. 1 after NaOH leaching.
FIG. 5 is a vertical cross section through an exemplary methanation cell in which the catalyst of the present invention may be used.

The appearance of mesh (14) at this stage is shown in FIG. 2. An enlarged cross section (250x) of a strand of treated Ni-12Mo expanded metal is shown in FIG. 3 and a 750x enlargement of the porous Raney surface coating is shown in FIG. 4. In these, it is seen that the Beta structured Raney Ni-12Mo layer is about three times as thick as the underlying Gamma layer. Since the predominant Beta layer is the outer layer which will be in contact with any medium in which the coated core is placed and is what serves to control the catalytic activity of the coating, the structure shown in FIGS. 3 and 4 is collectively called a Beta Raney Ni-12Mo coating.

After the selective leaching, the active nickel alloy coatings may exhibit a tendency to heat up when exposed to air. If uncontrolled, this self-heating or pyrophoric tendency can easily lead to problems with coating ignition with consequent severe damage to the coating. However, chemically treating (24) the porous nickel alloy layer has been found to eliminate this problem. Convenient methods for this chemical treatment include immersing the porous nickel alloy for between at least 1 hour and 4 hours in a dilute aqueous solution of an oxidant containing, for example, by weight either (a) 3 percent $NaNO_3$, or
(b) 3 percent $K_2Cr_2O_7$, or
(c) 3 percent $NaClO_3$ and 10 percent NaOH, or
(d) 3 percent $H_2O_2$.

This treatment safely eliminates the self-heating tendency of the porous nickel alloy surface without diminishing either its catalytic activity or mechanical properties.

Although the active porous nickel alloy surface layers, as prepared by the proceeding steps, have satisfactory mechanical properties and a low tendency to crack, compared with many of the Raney nickel surfaces of the prior art, the mechanical properties of the layer can be improved still further by optionally coating a very thin layer of nickel onto the porous surface (26). This nickel layer, which is preferably 5 to 10 microns thick, can be applied from conventional electroless nickel or a nickel electroplating bath and enhances the mechanical strength of the porous nickel alloy layer without diminishing its catalytic activity.

Methanation Studies

Referring now to FIG. 5, an exemplary methanation reactor (100) is shown in a cross-section in which a catalyst of this subject invention can be used. As shown, it comprises at least one reaction chamber (112) into which a plurality of layers (114) of catalyst (5) are loosely stacked, said layers being arranged so that the open structure of the mesh substrate is randomly oriented. A scrubbed mixture of hydrogen, and a gaseous carbon-bearing material such as carbon monoxide, carbon dioxide or a mixture thereof is admitted to the interior of reactor (100) through gas inlet (116). To insure that the reaction is driven to completion, a relatively large excess of hydrogen is normally used, typically being in the range of between about 3 to about 9 parts of $H_2$ per part of carbon-bearing material. The entering gas mixture passes through annulus (117) which is between discharge tube (118) and inner jacket (120) to enter the top of reaction chamber (112) and pass therethrough, contacting catalyst (5) and reacting enroute. The open structure presents a relatively low impedance to the gas so that the observed pressure drop through the reactor is quite small. This low pressure drop combined with the high reactivity of the catalyst allows extremely high gas-flow rates through the system.

The reaction products pass first through porous filter (122) in the bottom of reaction chamber (112) to remove any solid particles present and then leave the reactor through discharge tube (118) and gas outlet (124). Such an arrangement allows the incoming gas to be heated while the reaction products are cooled to prevent reversing the reaction of equations (1) and (2), supra. The overall reactor system is surrounded by an outer pressure jacket (126) which is sealingly mated with coupling (128) to hold all the parts in alignment and keep the system pressure tight. Temperatures within the reactor are measured by thermocouple (130). After the gases pass out of reaction chamber (112), they are fed into a recovery system (not shown) wherein the methane and any other higher hydrocarbons formed are separated and recovered from the reactants. Unreacted materials, mostly hydogen, may be recycled back into the reactor as fresh feedstock.

The catalyst of the present invention is readily adaptable to gas systems containing mixtures of hydrogen with either CO, $CO_2$ or a mixture thereof so that a wide range of starting materials can be used. For example, the carbon oxide starting material can be derived from the controlled combustion of coal or similar materials in either specially designed reactors or from the scrubbed smoke stack effluents from power stations, steam generators and similar carbon based fuel-burning applications. Hydrogen can be derived either from the electrolysis of water or conveniently obtained from the output of electrolytic chlor-alkali cells which typically give off large quantities of hydrogen as a by-product.

As shown, reactor (100) does not have an inherent or self-heating capability to start the reaction. Rather, it is adapted to have external heating means, such as a furnace (not shown), placed around it so as to provide a controlled source of heat to the gases flowing in annulus (117) and to allow overall temperature of the system to be slowly raised until the gases start to react in reaction chamber (112). This usually happens at between 150° C. and 170° C. In large applications, this temperature could be reached by preheating the incoming gases prior to their entering the system. However, this temperature is achieved, the highly exothermic nature of the reaction usually supplies sufficient additional heat to quickly raise the system temperature to a point where essentially all of the carbon-bearing material in the heated gas stream is converted to methane, ethane and higher hydrocarbons. For the system shown, in an operating range of about 250° C. to about 270° C., it is found that the conversion of the carbon oxide material to methane is essentially complete with only minimal amounts of ethane and higher hydrocarbons being produced.

The reaction temperature of 250°–270° C. is substantially lower than is normally utilized for systems of this type. Further, when applied with an overall system pressure of between about 50 and about 100 p.s.i., reaction of the carbon-bearing materials to form methane is exceptionally high. These pressure values are also substantially lower than normally utilized for systems of this type.

Operating at such a low pressure is highly advantageous since it permits a considerable economy in the design of a full-sized system for methanation as described herein. It has been found, however, that higher system pressures seem to promote the production of significant quantities of ethane and higher hydrocarbons in the reaction mass. Such a situation would appear to allow considerable flexibility in the nature of the final product or products produced.

Utilizing the apparatus of FIG. 5, an equilibrium or isothermal condition was quickly established which was sustained, without difficulty, for as long as 36 hours without a need to internally cool the reacting gases. It was further found that the problems noted in the prior art in stabilizing the reactor to prevent either the formation of coke and consequent plugging of the catalyst surface or the reverse did not occur. This is because the extremely high rate of gas-flow through the catalyst and the heat sinking of the relatively high percentage of excess hydrogen set up conditions wherein the reaction is essentially self-quenching once it passes through the catalyst stack.

Figure 7:
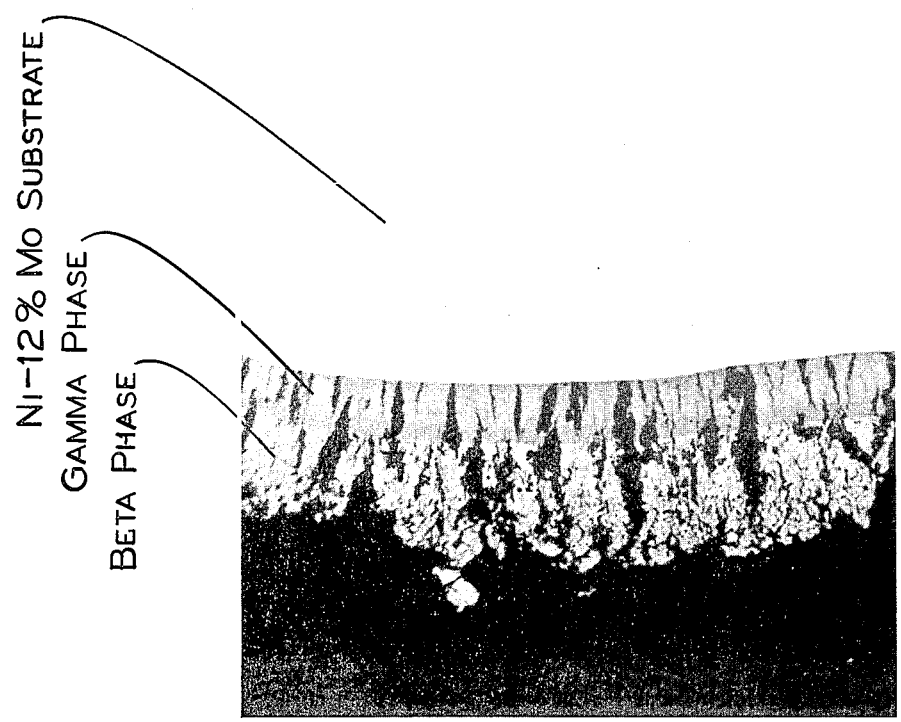
FIG. 7 is a 750x enlargement of a section of the Raney coating of FIG. 6.
Figure 6:
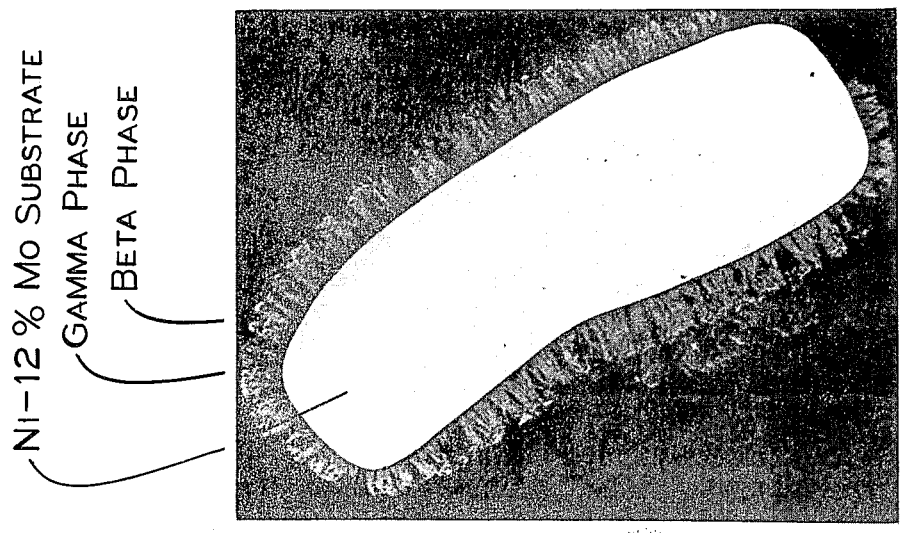
FIG. 6 is a 150x photomicrograph of the catalyst of FIG. 2 as it appeared after 307 hours use showing the Raney coating still largely intact with substantially no coke formation on the coating.

FIG. 6 is a photograph of a 150x enlargement of a strand of the catalyst of the present invention after 307 hours of use in the methanation reactor of FIG. 5. FIG. 6 shows that the surface is substantially free of carbon and that the overall thickness of the strand has not been materially reduced from its thickness prior to use. These effects are more clearly shown in FIG. 7 which is a photograph of a 750x magnification of the coating of FIG. 6.

One problem frequently encountered with many catalysts is their high sensitivity to sulfur contamination in either the form of $H_2S$ or $SO_2$ in the inlet gases. In commercial Raney nickel catalysts, tolerance values as low as 0.1 part per million are frequently found. The catalyst of this invention operates in the presence of a substantially higher value of sulfur in either form as compared to commercial catalysts now in use without poisoning the catalyst for continued use.

The following examples are given to illustrate the invention and are not deemed to be limiting thereof. All parts and percentages are by weight unless otherwise specified.

EXAMPLE 1

A catalyst was prepared as follows:

One inch diameter discs of about 0.015 inch thick Ni-12Mo alloy which had been expanded to a mesh having a diamond cell structure with dimensions of about 0.2 inch by 0.3 inch on a side was thoroughly cleaned by degreasing with acetone, lightly etching with 10 percent HCl, rinsing with water and, after drying, grit-blasting with No. 24 grit $Al_2O_3$ at a pressure of 3.4 kg/$CM^2$ (50 p.s.i.).

The cleaned nickel aluminum alloy discs were aluminized by applying a commercial flux and then dipping in a pot of molten aluminum at 675° for 1 minute to entirely coat the discs with aluminum. The aluminized discs were then heat-treated at 725° for 15 minutes in a nitrogen atmosphere to interdiffuse the nickel alloy and aluminum. After heat-treating, the discs were allowed to cool in a current of nitrogen for about 2 hours which produced a predominantly Beta phase structured, interdiffused layer on the surface.

The discs were then subjected to a leaching treatment in which the aluminum was selectively removed from the interdiffused layer to form an active porous nickel-molybdenum surface on the discs. The leaching treatment consisted of immersing the interdiffused discs in 20 percent NaOH at 80° C. for approximately 1 hour to dissolve away the excess aluminum and expose the catalytically active Beta phase. After leaching, the catalyst discs were first washed to remove loose material and then placed in the reactor of FIG. 5 while still wet and dried in a stream of hydrogen. They were then activated by continuing the flow of hydrogen at a temperature of about 300° C. for about 16 hours.

EXAMPLE 2

Using the catalyst of Example 1 and the reactor of FIG. 4, a disc stack height of about 2 inches having a total catalyst content of about 12 grams and solid volume of about 1.6 cc was assembled in reaction chamber (112). An 8:1 mixture of hydrogen and CO at a pressure of 180 p.s.i. was admitted at a flow rate of about 1350 cc per minute. This produced a space velocity of about 50,625 hours$^{-1}$ or about 6,750 cc per gram-hour.

Starting at a room temperature, the temperature of the reactor was gradually raised with samples being periodically taken to monitor the progress of the reaction. The results obtained are given in Table I. They show that the reaction began at a temperature of about 200° C. and that at a temperature of about 265° to 270° CO to hydrocarbon conversion was approaching 100 percent. The reactor was run in an isothermal mode for another 4 to 6 hours after which the reaction was terminated. Analyses of the output gases showed that above 265° C. the conversion of CO was essentially complete with about 95 percent going into $CH_4$ and about 5 percent going into $C_2H_6$ and "other" products which were unidentified. At a temperature of about 350° C., only $CH_4$ was produced. Examination of the catalyst showed essentially no carbon buildup or other source of degradation.

TABLE I

| TEMP (C.)* | % CONVERSION | % YIELD | | |
|---|---|---|---|---|
| | | $CH_4$ | $C_2H_6$ | "OTHER" |
| 140 | 0 | 0 | 0 | 0 |
| 170 | 0.08 | 0.08 | 0 | 0 |
| 190 | 0.92 | 0.92 | 0 | 0 |
| 200 | 6.62 | 3.31 | 1.65 | 1.66 |
| 210 | 19.32 | 11.47 | 3.93 | 3.92 |
| 230 | 25.04 | 14.76 | 5.14 | 5.14 |
| 265 | 98.91 | 94.18 | 2.36 | 3.37 |
| 300 | 99.54 | 94.63 | 2.46 | 2.45 |
| 330 | 99.58 | 94.61 | 2.48 | 2.49 |
| 350 | 99.54 | 99.54 | 0 | 0 |

*Pressure 180 p.s.i.

EXAMPLE 3

The method of Example 2 was repeated with the $H_2$:CO ratio being decreased to a value of 4:1. The results obtained with this higher CO concentration were substantially the same as those of Example 2.

EXAMPLE 4

The method of Example 2 was repeated except that the reactor pressure was 50 p.s.i. While the 100 percent reaction temperature of 270° C. was substantially the same as with higher pressure operation, analyses of the output gases showed that all of the CO was converted to $CH_4$ with no traces of $C_2H_6$ or other hydrocarbons being observed. Results of this run are given in Table II.

TABLE II

| TEMP (C.)* | % CONVERSION | % YIELD | | |
|---|---|---|---|---|
| | | $CH_4$ | $C_2H_6$ | "OTHER" |
| 160 | 0 | 0 | 0 | 0 |
| 180 | 0.18 | 0.18 | 0 | 0 |
| 200 | 0.99 | 0.99 | 0 | 0 |
| 210 | 2.31 | 2.31 | 0 | 0 |
| 220 | 3.55 | 3.55 | 0 | 0 |
| 230 | 7.79 | 7.79 | 0 | 0 |
| 245 | 15.51 | 15.51 | 0 | 0 |
| 260 | 97.46 | 97.46 | 0 | 0 |
| 265 | 99.19 | 99.19 | 0 | 0 |
| 270 | 99.23 | 99.23 | 0 | 0 |

*Pressure 50 p.s.i.

EXAMPLE 5

The method of Example 2 was repeated with the CO being replaced by $CO_2$. The results obtained were substantially the same as those in Example 2.

EXAMPLE 6

The method of Example 2 was repeated with the incoming gas being a mixture of $H_2$, CO and $CO_2$ in a ratio of about 8:1:1. It was found that the conversion of both gases was nearly 100 percent at 260° C. to 270° C. with substantially all of the reaction product being $CH_4$. The results obtained are illustrated in FIG. 8.

Comparative Example A

Using a commercial granular $Al_2O_3$ supported Raney Ni-Mo catalyst (Davison 3000) and the reactor of FIG. 5, 4.9678 grams of catalyst having a total volume of 8.998 cc were placed in the reaction chamber. An 8:1 mixture of $H_2$ and CO at a reactor pressure of 100 p.s.i.g. was admitted at a flow rate of 758.3 cc per minute. This produced a space velocity of about 50564.57 hours$^{-1}$ or about 9158.58 cc per gram-hour.

Figure 8:
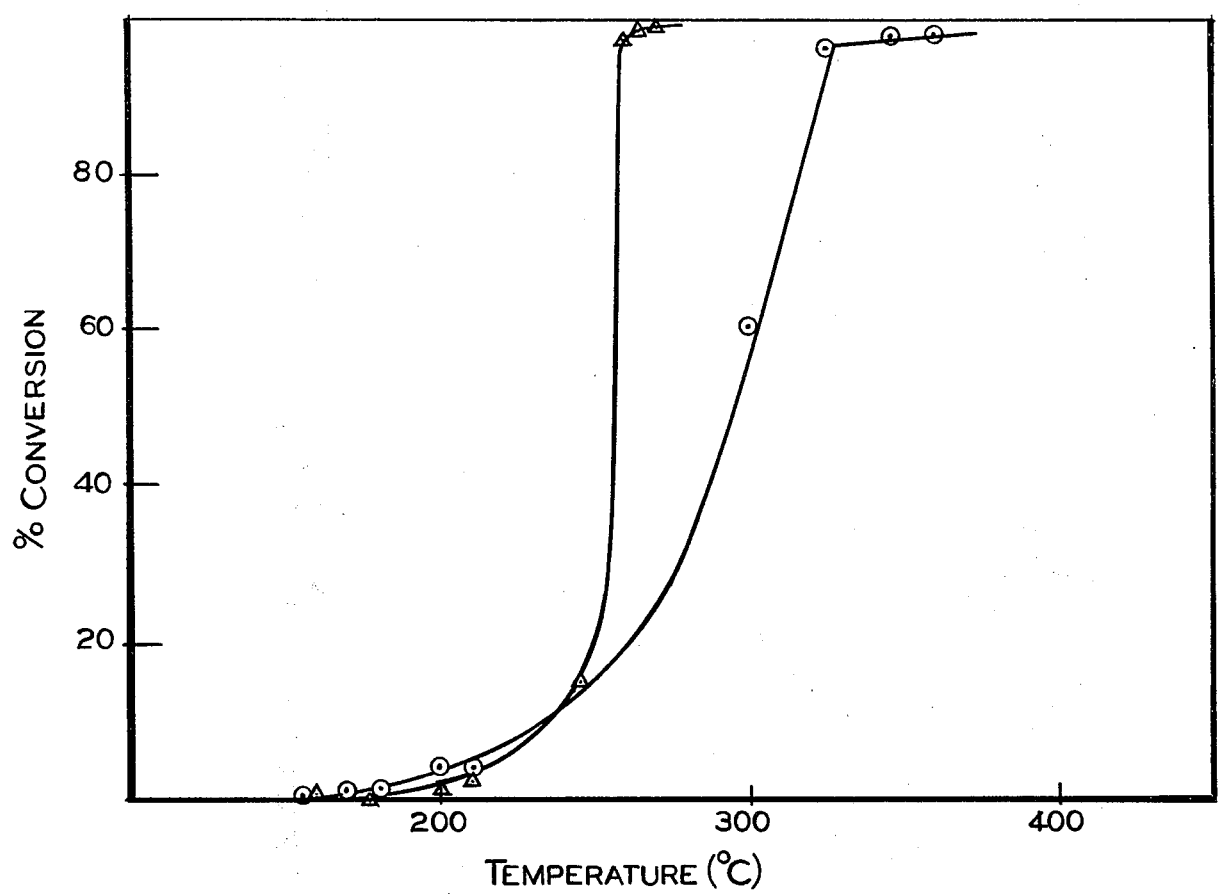
FIG. 8 is a comparison of the response of an Ni-Mo catalyst according to the present invention with the effectiveness of a commercially available $Al_2O_3$ supported, molybdenum promoted granular Raney nickel catalyst for the methanation of CO.

The method of Example 2 was then repeated with the results shown in Table III and FIG. 8. The reaction initiated about 190° and did not achieve substantially complete CO conversion until a temperature in excess 325° C. was obtained. The results of Example 6 are plotted with these data to provide a more direct comparison with the catalyst of this invention.

TABLE III

| TEMP (C.)* | % CONVERSION | % YIELD | | |
|---|---|---|---|---|
| | | $CH_4$ | $C_2H_6$ | $C_3H_8$ |
| 155 | 0 | 0 | 0 | 0 |
| 175 | 0.45 | 0.45 | 0 | 0 |
| 185 | 1.05 | 1.05 | 0 | 0 |
| 200 | 5.54 | 5.54 | 0 | 0 |
| 210 | 5.63 | 5.63 | 0 | 0 |
| 325 | 99.3 | 99.3 | 0 | 0 |
| 345 | 99.48 | 99.48 | 0 | 0 |
| 360 | 99.5 | 99.5 | 0 | 0 |

*Pressure 100 p.s.i.

EXAMPLE 7

Using the method of Example 1, a Raney mesh catalyst having 5 percent Ru was fabricated. This was assembled in the reactor of FIG. 5 and the method of Example 2 repeated with a reactor pressure of 100 p.s.i.

Analyses of the output gases as shown in Table IV. The reaction was initiated at a temperature of about 200° C. with a substantially 100 percent conversion of the CO at a temperature of 338° C. At temperatures above about 215° C., ethane is produced and at temperatures above 260° C., propane is produced.

TABLE IV

| TEMP (C.)* | % CONVERSION | % YIELD | | | |
|---|---|---|---|---|---|
| | | CH$_4$ | C$_2$H$_6$ | C$_3$H$_8$ | "OTHER" |
| 170 | 0 | 0 | 0 | 0 | 0 |
| 200 | 0.56 | 0.56 | 0 | 0 | 0 |
| 215 | 2.03 | 1.4 | 0.31 | 0 | 0.32 |
| 225 | 4.75 | 3.45 | 0.65 | 0 | 0.65 |
| 235 | 7.37 | 5.46 | 0.96 | 0 | 0.95 |
| 245 | 11.64 | 8.46 | 1.59 | 0 | 1.59 |
| 260 | 26.17 | 19.1 | 3.4 | 0.09 | 3.58 |
| 300 | 88.33 | 78.45 | 2.22 | 1.81 | 5.85 |
| 320 | 91.84 | 82.96 | 1.62 | 1.88 | 5.38 |
| 338 | 99.72 | 94.53 | 0.25 | 1.57 | 3.37 |

*Pressure 100 p.s.i.

EXAMPLE 8

The method of Example 7 was repeated with CO$_2$ and reactor pressures of 100 and 200 p.s.i. with the results shown in Tables V and VI, respectively. It is interesting to note that although higher temperatures were used, no traces of ethane or propane were observed in either run when CO$_2$ was the starting gas.

TABLE V

| TEMP (C.)* | % CONVERSION | % YIELD | | |
|---|---|---|---|---|
| | | CH$_4$ | C$_2$H$_6$ | C$_3$H$_8$ |
| 225 | 0.68 | 0.68 | 0 | 0 |
| 245 | 1.43 | 1.43 | 0 | 0 |
| 255 | 2.98 | 2.98 | 0 | 0 |
| 275 | 4.4 | 4.4 | 0 | 0 |
| 310 | 14.1 | 14.1 | 0 | 0 |
| 365 | 63.12 | 63.12 | 0 | 0 |
| 390 | 75.34 | 75.34 | 0 | 0 |
| 420 | 84.74 | 84.74 | 0 | 0 |
| 440 | 90.54 | 90.54 | 0 | 0 |
| 475 | 96.45 | 96.45 | 0 | 0 |

*Pressure 100 p.s.i.

TABLE VI

| TEMP (C.)* | % CONVERSION | % YIELD | | |
|---|---|---|---|---|
| | | CH$_4$ | C$_2$H$_6$ | C$_3$H$_8$ |
| 235 | 1.21 | 1.21 | 0 | 0 |
| 250 | 2.59 | 2.59 | 0 | 0 |
| 275 | 5.9 | 5.9 | 0 | 0 |
| 310 | 15.5 | 15.5 | 0 | 0 |
| 350 | 47.24 | 47.24 | 0 | 0 |
| 390 | 77.99 | 77.99 | 0 | 0 |
| 395 | 77.71 | 77.71 | 0 | 0 |
| 415 | 86.01 | 86.01 | 0 | 0 |
| 435 | 91.79 | 91.79 | 0 | 0 |
| 460 | 99.48 | 99.48 | 0 | 0 |

*Pressure 200 p.s.i.

EXAMPLE 9

The method of Example 2 was repeated with the incoming gas being contaminated by 24 parts per million of H$_2$S. After a temperature of 200° C. was reached, the reaction was continued at that temperature until a total run-length of 27 hours was achieved, during which time some 4.7×10$^7$ ppm sulfur passed over the catalyst. Analyses of the output gas showed no decrease in the activity of the catalyst or change in the composition of the reaction products.

EXAMPLE 10

The method of Example 2 was repeated with a contamination of 500 parts per million of SO$_2$ being added to the input gas. After a temperature of about 200° C. was reached, the reaction was continued at that temperature until a total run-length of 49 hours was achieved, during which time a total of 1.7×10$^9$ ppm sulfur passed over the catalyst. Analyses of the output gases showed a gradual reduction in conversion rate reaching a value of about 40 percent by the end of the run but essentially no change in the composition of the reaction products.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A monolithic catalyst comprised of a metallic substrate with an integral Raney metal exterior surface, said surface being predominantly derived from an adherent Ni$_x$M$_{1-x}$Al$_3$ Beta structured crystalline precursory layer, where said layer is integral with and derived from said substrate, M is a catalytic enhancer selected from the group consisting of molybdenum, titanium, tantalum, ruthenium or mixtures thereof and where x, the weight fraction of nickel in the combined weight of Ni and M, is within the range of from about 0.80 to about 0.95.

2. The catalyst of claim 1 wherein said catalyst enhancer is molybdenum.

3. The catalyst of claim 1 wherein said catalyst enhancer is ruthenium.

4. The catalyst of claim 1 wherein said catalyst enhancer is tantalum.

5. The catalyst of claim 1 wherein said catalyst enhancer is titanium.

6. The catalyst of claim 2 wherein x is between about 0.82 and about 0.90.

7. The catalyst of claim 3 wherein x is between about 0.90 and about 0.95.

8. The catalyst of claim 1 wherein said substrate is a perforated metal.

9. The catalyst of claim 8 wherein said substrate is expanded mesh.

10. The catalyst of claim 9 wherein said substrate is a metallic screen.

* * * * *